United States Patent [19]

Sachse et al.

[11] Patent Number: 5,128,797
[45] Date of Patent: Jul. 7, 1992

[54] NON-MECHANICAL OPTICAL PATH SWITCHING AND ITS APPLICATION TO DUAL BEAM SPECTROSCOPY INCLUDING GAS FILTER CORRELATION RADIOMETRY

[75] Inventors: Glen W. Sachse, Yorktown; Liang-Guo Wang, Hampton, both of Va.

[73] Assignee: The United States of America as represented by the Administrator of the National Aeronautics and Space Administration, Washington, D.C.

[21] Appl. No.: 653,605

[22] Filed: Feb. 11, 1991

[51] Int. Cl.$^5$ .............................................. G02F 1/01
[52] U.S. Cl. ...................................... 359/246; 356/370; 356/414; 359/247; 359/281
[58] Field of Search ....................... 350/385, 403, 404; 356/360, 368, 414, 415, 370; 359/246, 247, 252, 281, 287

[56] References Cited

U.S. PATENT DOCUMENTS

| | | | |
|---|---|---|---|
| 3,586,416 | 6/1971 | DeBitetto | 350/385 |
| 3,638,024 | 1/1972 | Chen et al. | 350/385 |
| 3,738,755 | 6/1973 | Chaney | 356/368 |
| 3,738,756 | 6/1973 | Chaney | 356/368 |
| 3,900,247 | 8/1975 | Zaky | 350/385 |
| 4,105,337 | 8/1978 | Bjorklund et al. | 350/403 |
| 4,108,555 | 8/1978 | Helder et al. | 356/414 |
| 4,740,061 | 4/1988 | Miura | 350/381 |
| 4,759,628 | 7/1988 | Tatsuno et al. | 356/360 |
| 4,845,356 | 7/1989 | Baker | 356/368 |

FOREIGN PATENT DOCUMENTS

0361064  4/1990  European Pat. Off. .

OTHER PUBLICATIONS

Morrow, W. H. and Nicholls, R. W., "Some Recent Measurements . . . with Gas Filter Correlation Spectrometers, Gascofil and Gascosan", Optical Remote Sensing of the Atmosphere, 1990 Technical Digest Series, vol. 4, Feb. 12-15, 1990, Incline Village, Nev., pp. TuD15-1/332 to TuD15-4/335.

Henry G. Richle, Jr. et al, "Middle and Upper Tropospheric Carbon Monoxide Mixing Ratios as Measured by a Satellite-Borne Remote Sensor During Nov. 1981", J. Geophysical Research, vol. 91, No. C9, Sep. 30, 1986, pp. 10,865 to 10,887.

Henry G. Richle, Jr., "TRACER A Multi-Level Tropospheric Carbon Monoxide Correlation Radiometer for Eos." Optical Remote Sensing of the Atmosphere, 1990 Technical Digest Series, vol. 4, Feb. 12-15, 1990, Incline Village, Nev., pp. MB5-1/40 to MB5-4/43.

Primary Examiner—Bruce Y. Arnold
Assistant Examiner—Martin Lerner
Attorney, Agent, or Firm—Kevin B. Osborne

[57] ABSTRACT

A non-mechanical optical switch is provided for alternately switching a monochromatic or quasi-monochromatic light beam along two optical paths. A polarizer polarizes light into a single, e.g., vertical component which is then rapidly modulated into vertical and horizontal components by a polarization modulator. A polarization beam splitter then reflects one of these components along one path and transmits the other along the second path. In the specific application of gas filter correlation radiometry, one path is directed through a vacuum cell and one path is directed through a gas correlation cell containing a desired gas. Reflecting mirrors cause these two paths to intersect at a second polarization beam splitter which reflects one component and transmits the other to recombine them into a polarization modulated beam which can be detected by an appropriate single sensor.

21 Claims, 5 Drawing Sheets

NON-MECHANICAL OPTICAL PATH SWITCHING AND ITS APPLICATION TO DUAL BEAM SPECTROSCOPY INCLUDING GAS FILTER CORRELATION RADIOMETRY

ORIGIN OF THE INVENTION

The invention described herein was made jointly in the performance of work under Contract NAS1-18344 and an employee of the United States Government. In accordance with 35 U.S.C. 202, the contractor elected not to retain title.

BACKGROUND OF THE INVENTION

1. Technical Field of the Invention

The present invention relates to non-mechanical optical path switching and its application to dual beam spectroscopy including gas filter correlation radiometry.

2. Discussion of the Related Art

Non-mechanical optical path switching has many potential applications particularly in the field of dual beam spectroscopy. In dual beam spectroscopy, light from a radiation source is divided between two optical paths. Each optical path generally contains some medium through which the radiation is transmitted and thus partially absorbed. The key measurement in this type of spectroscopy is related to the difference in optical transmission between the two paths for the incident radiation. Although the gas filter correlation radiometer (GFCR) is but one example of a dual beam spectrometer, for illustrative purposes this application will be discussed in detail.

Gas filter correlation radiometers (GFCRs) may remotely infer the concentration of a gas species along some external path. In many GFCRs gas sensing is accomplished by viewing through two optical cells the emission/absorption of the gas molecules along the external path. These two optical cells, often called the correlation and vacuum cells, correspond to the media found in the two optical paths of a dual beam spectrometer. The correlation cell contains a high optical depth of a gas species i and thus strongly absorbs radiation at the molecular transition wavelengths of the particular gas. In effect the correlation cell acts as a spectral "notch filter", the spectral notches being coincident with the band structure of gas species i. On the other hand, the vacuum cell encloses either a vacuum or a gas that is non-absorbing in the spectral region of interest. The difference signal $\Delta S$ between these two views of the emitting/absorbing gas species i can be related to the concentration of this gas along a path external to the GFCR.

Figure 1:
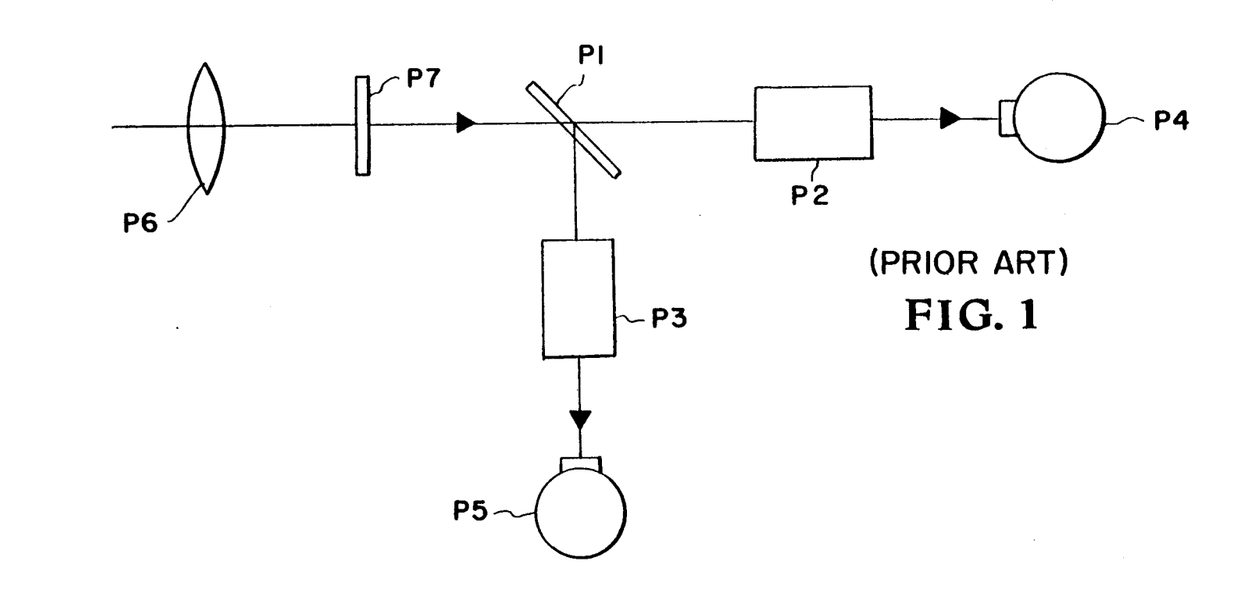
FIG. 1 is a schematic representation of a conventional GFCR using a beam splitter and two detectors.
Figure 2:
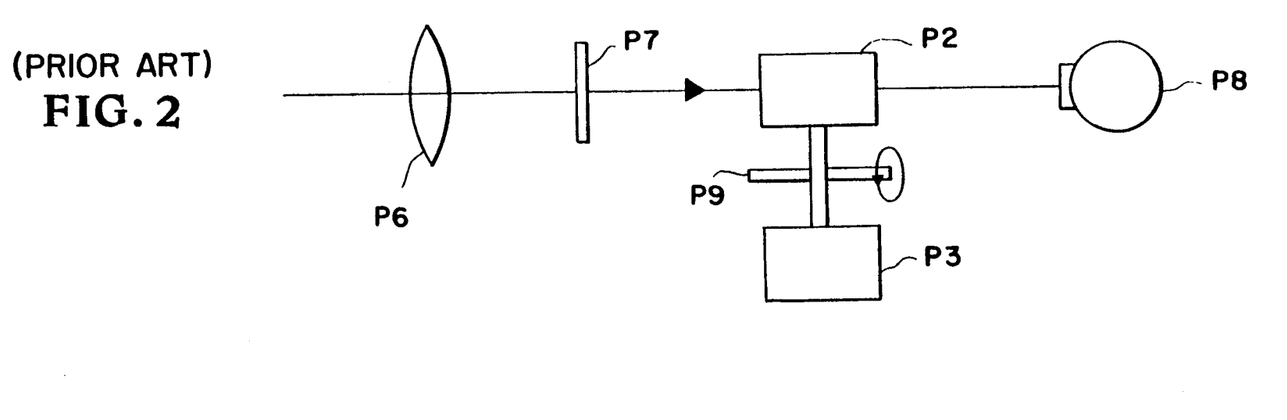
FIG. 2 is a schematic representation of a conventional GFCR using a mechanical wheel and a single detector.

In one known GFCR shown in FIG. 1, the radiation is divided by a simple beam splitter P1 into two paths—one containing a correlation cell P2 and the other a vacuum cell P3. The difference signal $\Delta S$ is derived from the difference in the outputs of two detectors P4 and P5 respectively located at the end of the two optical paths. Suitable collecting optics P6 and an interference filter P7 are provided to collect and spectrally filter the light. In other GFCRs, the critical $\Delta S$ is derived from a single detector P8, as shown in FIG. 2. In this case, the $\Delta S$ is generated by physically moving the correlation and vacuum cells P2 and P3 periodically in front of the GFCR detector. This is often accomplished by mounting the correlation and vacuum cells on a rapidly rotating wheel P9 so that they alternately pass in and out of the single optical path.

The first GFCR approach of FIG. 1 uses two detectors to derive the small $\Delta S$ signal. GFCR measurements of gas concentration are extremely sensitive to minute drifts in the response of the two detectors which must be frequently and precisely balanced. Also, surface response inhomogeneities on the two detectors can lead to significant measurement errors if the radiation background being viewed by the GFCR is spatially inhomogeneous. Such a situation may occur, for example, in an aircraft or satellite nadir viewing application.

The single detector approach of FIG. 2 has the disadvantage that some mechanical means must be used to alternate the view of the detector through the correlation and vacuum cells. Although this mechanical optical path switching may occur rapidly on the order of 100 Hz, it may nevertheless limit the GFCR performance in certain demanding applications where the background radiation varies rapidly, e.g., in some nadir earth-viewing cases. In applications where instrument maintenance is restricted or impossible, such as satellite applications, the presence of rapidly moving instrument components is an important constraint as it may limit operational lifetime. Angular momentum compensation must also be addressed especially for satellite applications.

OBJECTS OF THE INVENTION

It is accordingly an object of the present invention to provide a non-mechanical optical switch for various applications requiring two optical paths.

It is another object of the present invention to perform dual beam spectroscopy such as gas filter correlation radiometry in which the difference signal $\Delta S$ can be obtained from only one detector thus reducing measurement errors and balancing requirements.

It is still another object of the present invention to switch the view of a single detector through a correlation cell and a vacuum cell non-mechanically.

It is a further object of the present invention to accomplish such switching more quickly.

It is yet another object of the present invention to accomplish the foregoing objects with an apparatus requiring low maintenance.

It is a further object of the present invention to accomplish the foregoing objects without generating angular momentum in any system component.

Additional objects and advantages of the present invention are apparent from the specification and drawings which follow.

SUMMARY OF THE INVENTION

The foregoing and additional objects are obtained by a non-mechanical optical path switch according to the present invention which comprises a polarizer, polarization modulator and a polarization beam splitter. The polarizer polarizes light from a light source into a single, e.g., vertically polarized, component which is then rapidly modulated into alternate vertically and horizontally polarized components by the polarization modulator. The polarization modulator may be used in conjunction with optical waveplates. The polarization modulated beam is then incident on the polarization beam splitter which transmits light of one orthogonal component, e.g., horizontally polarized, and reflects light of a perpendicular component, e.g., vertically polarized. In a gas filter correlation radiometer application, the transmitted horizontally polarized beam is reflected by a mirror, passes through a gas correlation cell, and is transmitted through a second beam splitter. The reflected vertically polarized beam passes through a vacuum cell, is reflected by a mirror and then reflected by the second beam splitter. The second beam splitter recombines the horizontal and vertical components into a single beam which is read by a single conventional detector.

DETAILED DESCRIPTION OF THE PREFERRED EMBODIMENTS

Figure 3:
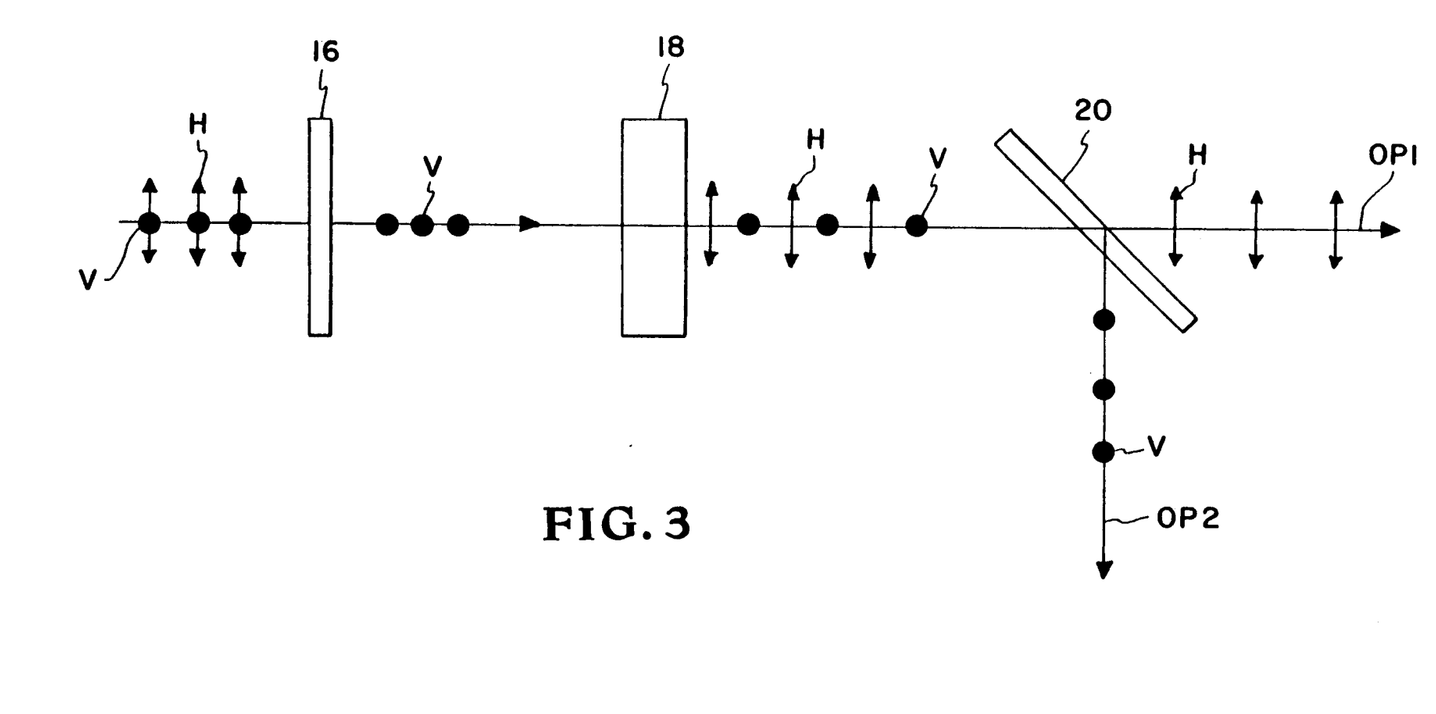
FIG. 3 is a schematic representation of a non-mechanical optical path switch according to the present invention.

Referring now to FIG. 3, the non-mechanical optical path switch according to the present invention comprises the basic components of optical polarizer 16, polarization modulator 18, and polarization beam splitter 20. Such a switch can be used in numerous applications such as optical computing and dual beam spectroscopy which includes gas filter correlation radiometry. Unpolarized monochromatic or quasi-monochromatic light having vertically polarized components V and horizontally polarized components H from any radiation source, e.g., a thermal source, laser, etc., is first polarized by optical polarizer 16 into a single component, e.g., vertically polarized as in FIG. 3. The polarized radiation is then incident upon polarization modulator 18 which rapidly modulates the output polarization between vertical and horizontal components. This switch eliminates the need for rapidly moving mechanical parts, thereby eliminating maintenance requirements and angular momentum considerations.

Figure 4:
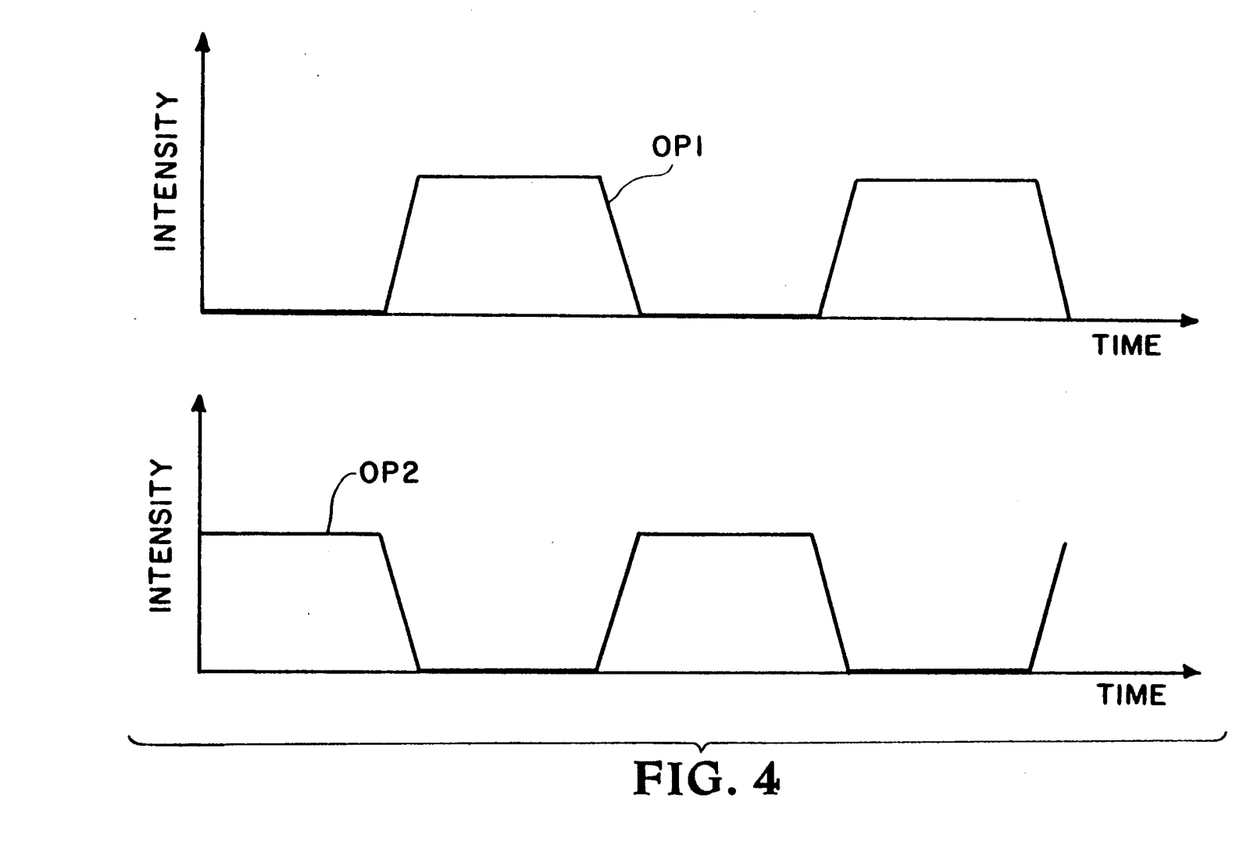
FIG. 4 is a graph showing the change in radiation intensity with time along two optical paths generated by the embodiment of FIG. 3.

Non-mechanical optical path switching occurs at polarization beam splitter 20. Specifically, polarization beam splitter 20 splits the beam along two paths OP1 and OP2 by transmitting one orthogonal beam component and reflecting the other orthogonal beam component. In the example shown, horizontal beam component H is transmitted along path OP1 and vertical beam component V is reflected along path OP2. Conversely, the vertical component may be transmitted and the horizontal component may be reflected by reorientation of beam splitter 20. The temporal change in radiation intensity for the two optical paths OP1 and OP2 is represented in FIG. 4 as the polarization is switched from vertical to horizontal in the specific embodiment shown in FIG. 3.

Figure 5:
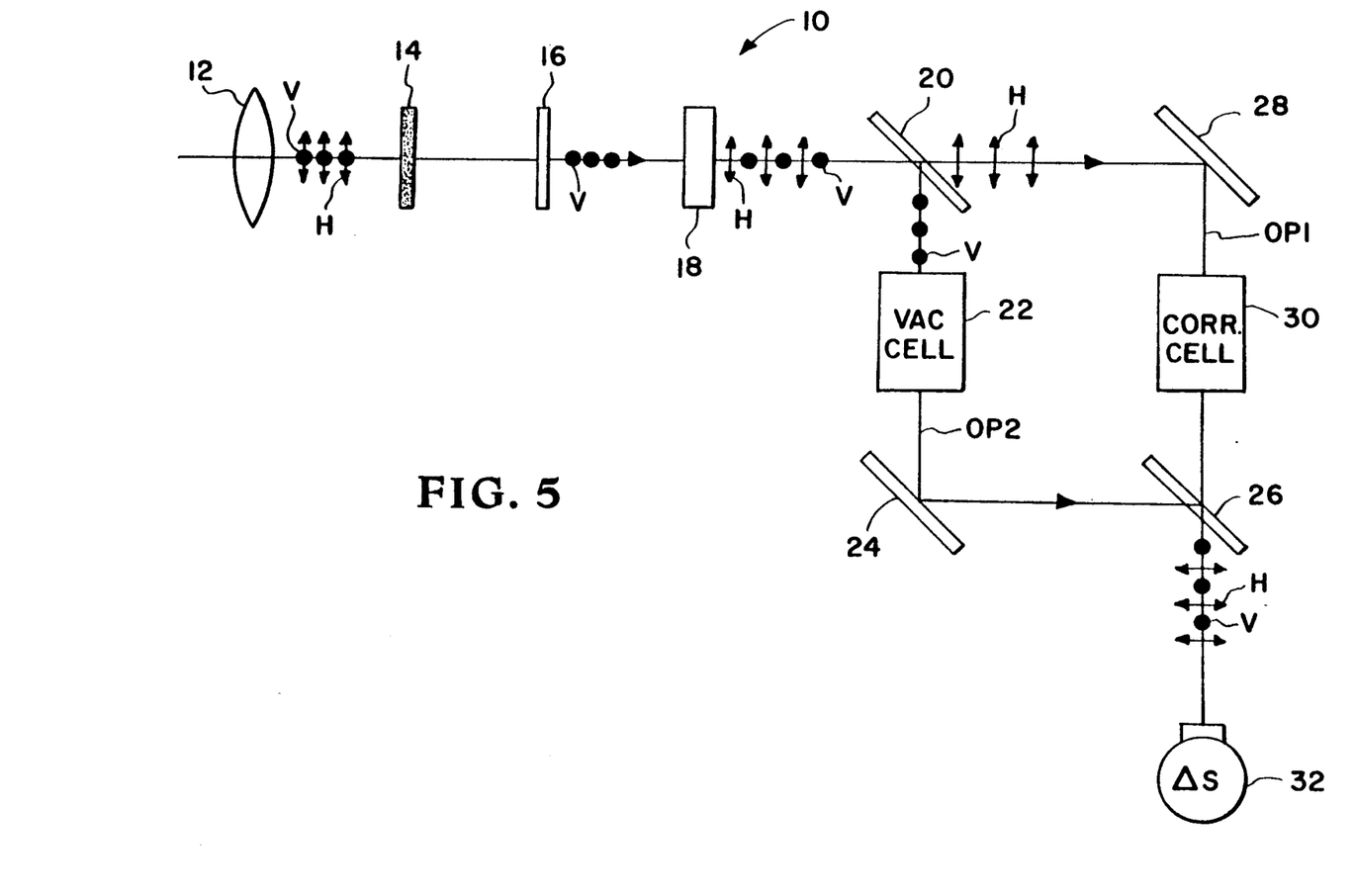
FIG. 5 is a schematic representation of a particular GFCR configuration using a non-mechanical optical path switch according to the present invention.

Referring now to FIG. 5, a gas filter correlation radiometer (GFCR) 10 is shown according to the present invention utilizing the above described optical path switch. Optics system 12, e.g., a telescope or other lens/mirror system, collects unpolarized light from a radiation source such as the earth and atmosphere when GFCR 10 is mounted on a satellite or aircraft, a blackbody when GFCR 10 is used as a laboratory or in-situ instrument, the sun, etc. This unpolarized light beam comprises vertically polarized components V and horizontally polarized components H. A spectral filter 14 is provided next to transmit only the portion of the optical spectrum of the beam which contains the transition lines of the particular gas species of interest, e.g., carbon monoxide (CO). Optical polarizer 16 is provided after spectral filter 14 and is aligned to polarize the incoming radiation in the desired directional component, e.g., vertically in the embodiment depicted in FIG. 3. A polarization modulator 18 then receives the incident vertically polarized beam and rapidly modulates the output beam between vertical and horizontal polarization. Depending on the measurement application, and the type of polarization modulator utilized, polarization modulation may be accomplished over a wide frequency range from near DC to radio frequencies (RF).

Polarization beam splitter 20 non-mechanically switches this polarization modulated output beam between two paths by transmitting the beam when it is horizontally polarized and reflecting it when it is vertically polarized. Alternatively, beam splitter 20 may be oriented so as to transmit vertically polarized light and to reflect horizontally polarized light.

Polarization beam splitter 20 thus alternately directs the beam along a correlation and a vacuum cell path. In the specific embodiment shown, beam splitter 20 is oriented to reflect the vertically polarized light so that it passes through a vacuum cell 22 containing a vacuum or a gas which is non-absorbing in the spectral region of interest. The exiting light is then reflected by mirror 24 so that it intersects a second polarization beam splitter 26. The optical path from the first beam splitter through the vacuum cell to the second beam splitter is designated the vacuum optical path. First beam splitter 20 transmits horizontally polarized light, which is then reflected by mirror 28 so that it passes through gas correlation cell 30 containing a high optical depth of the gas species of interest and is then incident on the second beam splitter 26. The optical path from the first beam splitter through the gas correlation cell to the second beam splitter is designated the gas correlation optical path and has the same length as the vacuum optical path.

In the more general case of dual beam spectroscopy, vacuum cell 22 and gas correlation cell 30 are replaced with a first medium and a second medium, which can include a reference or sample gas, liquid or solid.

Second beam splitter 26 can be selected to have the same transmitting and reflecting properties as first beam splitter 20, i.e., in the example shown it transmits the horizontally polarized light from the gas correlation optical path and reflects the vertically polarized light from the vacuum optical path. The orientation of the mirrors and the first beam splitter cause the two optical paths to intersect at the second beam splitter.

The second beam splitter may be oriented in the opposite sense to the first beam splitter, wherein the vertical components pass through and the horizontal components reflect to the right in FIG. 5, necessitating locating intensity sensor 32 to the right of the second beam splitter in FIG. 5. The beam is recombined into a single optical path having rapidly alternating vertical and horizontal components which are received and read by a single conventional intensity detector 32 to determine ΔS, i.e., the difference in the intensity between the horizontally and vertically polarized beams received at detector 32. In the specific application of an aircraft or satellite nadir-viewing GFCR, this difference signal is related both to the amount of gas in the cells and the height of that gas in the atmosphere or other test location. This ΔS value, a scene brightness measurement and a knowledge of certain atmospheric parameters such as the temperature profile are combined through a numerical radiative transfer program to allow an inference of the atmospheric mixing ratio of the particular gas. Also, any other conventional methods may be used to manipulate the data sensed by detector 32.

The non-mechanical optical path switching of the present invention accordingly allows a single detector to be used to arrive at ΔS thereby reducing balancing requirements and detector surface inhomogeneity problems. The present invention also enables a quick switching rate orders of magnitude greater than in conventional GFCRs between the vacuum optical path and the gas correlation path. The switching rate is determined by selection of the polarizing modulator as discussed below. This high speed optical path switching will greatly improve GFCR performance in demanding situations such as nadir earth-viewing applications from aircraft and spacecraft. The rapid switching in effect freezes the radiometer view of rapid background radiation variations. It also allows the GFCR field-of-view to be decreased to enable higher spatial resolution measurements. This narrowed field-of-view will increase the amount of data obtained in spacecraft applications since clear regions between cloud coverage are more likely to be found with finer spatial resolution. The lack of rapidly moving mechanical parts reduces maintenance concerns and eliminates angular momentum concerns.

The key components of the optical path switch are the polarizer, polarization beam splitter and polarization modulator. All are commercially available and some basic parameters for use in their selection for various applications are discussed in the following paragraphs. Since many of the component characteristics are wavelength dependent, the spectral region for a desired application is important in component selection.

Polarizer 16 can be eliminated if a polarized light source as a polarized laser is used. If necessary the polarizer 16 linearly polarizes the incoming radiation before it is incident on the polarization modulator 18. Important polarizer parameters include extinction ratio, transmission, and angular acceptance. Common polarizer types include prism, reflection, dichroic and wire grid polarizers. Prism and reflection polarizers exhibit high extinction ratios, but their poor angular acceptance limits their application. Dichroic and wire grid polarizers, on the other hand, possess wide angular acceptance. Dichroic polarizers in addition have high extinction ratios and are commercially available for the visible and near infrared region. Wire grid polarizers exhibit moderate extinction ratios and are available for infrared applications.

The purpose of the polarization beam splitter 20 is to separate the orthogonal polarization components of the radiation after the polarization modulator. Thus the loss and extinction ratio for both the transmitted and reflected radiation as well as angular acceptance must be considered. The same consideration must be applied to polarization beam splitter 26 which combines the two orthogonal polarizations in GFCR applications. Dichroic polarizers are not acceptable as polarization beam splitters since they strongly absorb one of the polarization components. Prism and reflection polarization beam splitters may only be used in applications where angular acceptance is not a primary concern. Wire grid polarizers with their large acceptance angle and moderate extinction ratios for both transmission and reflection are good polarization beam splitter candidates in the infrared.

Figure 6:
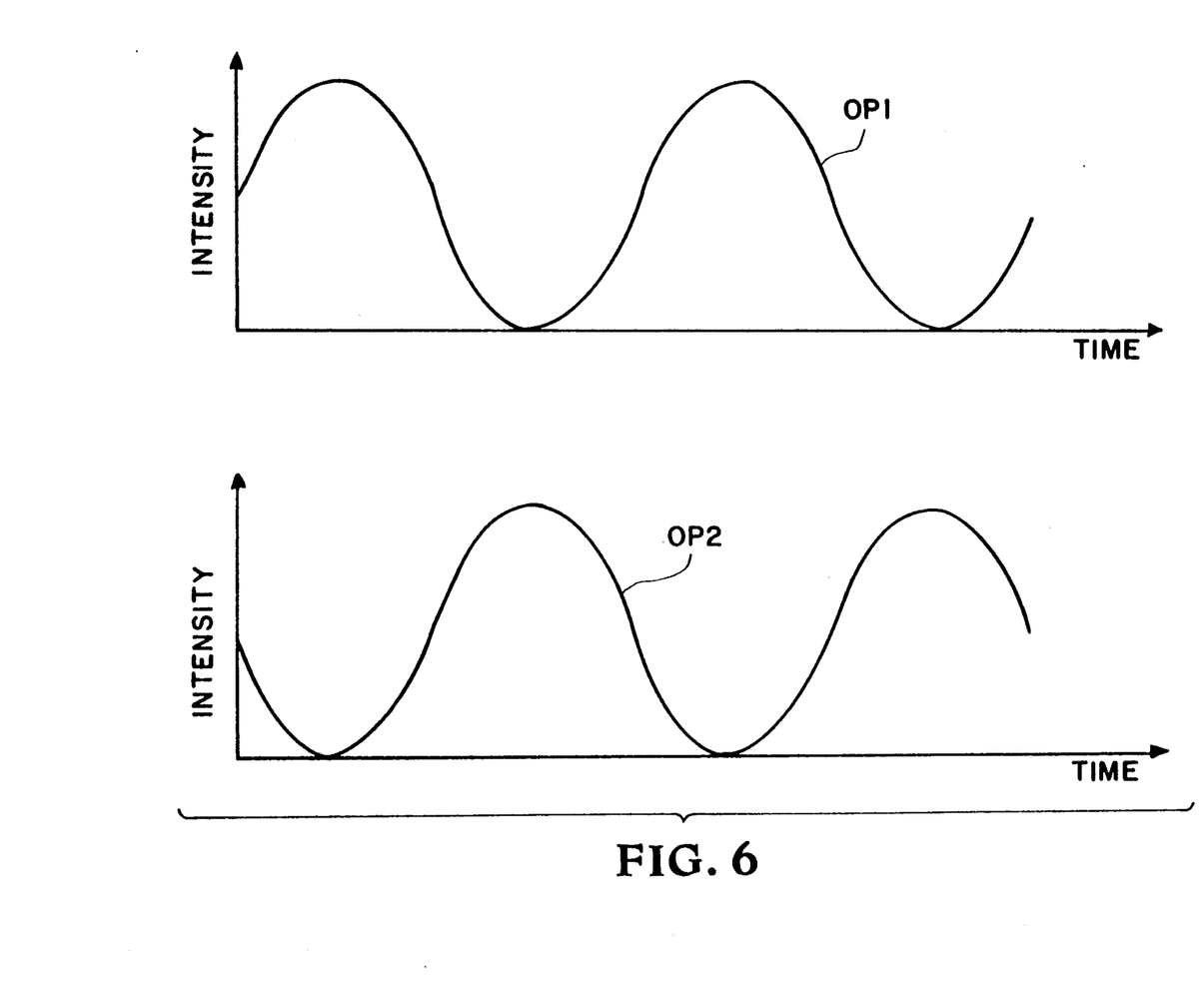
FIG. 6 is a graph showing a quasi-sinusoidal change in radiation intensity with time along two optical paths generated by a polarization modulator, e.g., a photoelastic modulator used in an embodiment of the present invention.

The polarization modulator 18, which may also be used in conjunction with a waveplate, alternatively modulates the state of polarization between two orthogonal linear polarizations (i.e., H and V). Important parameters include transmission loss and angular acceptance; and since the modulators are energized devices, energy consumption and heating effects are also important. Electro-optic and photo-elastic modulators are commercially available that operate over a wide spectral region including the UV, visible and infrared. Both modulator types generate a polarization change by modulating the birefringence of an optical crystal. In the electro-optic modulator a strong electric field is applied to yield the desired birefringence change, whereas in the photo-elastic modulator, mechanical stress introduced by a transducer attached to the optical crystal generates the birefringence change. The magnitude of the voltage applied to an electro-optic modulator for a given birefringence modulation increases with increasing optical wavelength. For this reason, modulators using the electro-optic effect are generally more suited for shorter wavelength applications, i.e., UV, visible, and near infrared. An advantage of electro-optic modulators is their wide electronic bandwidth which allows them to be modulated with a variety of electronic waveforms, such as the "quasi-square wave" polarization modulation shown in FIG. 4. Square wave or other polarization waveforms can be useful in some GFCR applications to approximate the switching or "chopping" achieved by the mechanical switching shown in FIG. 2. To reduce the driving power requirements of photo-elastic modulators, these devices are generally excited at the resonant frequency of the photo-elastic crystal. The photo-elastic modulators must accordingly be excited with a sinusoidal electronic waveform and the resulting polarization modulation may have a quasi-sine wave characteristic, as shown in FIG. 6. Photo-elastic modulators are commercially available for UV, visible and infrared applications. Crystal heating, the mechanical strength of the crystals and the loss of optical transmission are factors limiting longer wavelength applications. Other potential polarization modulators include magneto-optic devices possibly employing the Faraday or Kerr effects, liquid crystal devices (LCDs), etc.

Many modifications, substitutions and improvements will become apparent to one of skill in the art without departing from the spirit and scope of the present invention as described herein and defined in the following claims.

What is claimed is:

1. A method of performing dual beam spectroscopy to determine the concentration of a gas of interest in a particular quantity, comprising the steps of:

modulating a polarized light beam, which has passed through the gas of interest in the particular quantity, between two alternating orthogonal polarization components;

switching the polarization modulated beam by transmitting one orthogonal component along a first optical path and reflecting the other orthogonal component along a second optical path;

directing one optical path through a vacuum cell and directing the other optical path through a spectral notch filter having spectral notches which are coincident with the band structure of the gas of interest;

intersecting the first and second optical paths at an intersection point; combining the respective orthogonal polarization components of first and second optical paths at the intersection point into a polarization modulated beam having two alternatively orthogonal polarization components by transmitting one orthogonal component and reflecting the other orthogonal component; and sensing a difference in the intensity between the two alternating orthogonal polarization components of the combined beam as an indication of the spectral emission/absorption of the light by the gas of interest in the particular quantity, the spectral emission/absorption being indicative of the concentration of the gas of interest in the particular quantity.

2. the method according to claim 1, further comprising polarizing an unpolarized light beam prior to said modulating step.

3. The method according to claim 2, further comprising spectrally filtering a light beam prior to said modulating step to transmit only the portion of the optical spectrum of the beam which contains the transition lines of the gas of interest.

4. The method according to claim 1, wherein said intersecting step comprises reflecting the first optical path and reflecting the second optical path.

5. The method according to claim 1, wherein said sensing step comprises locating a single detector in said combined polarization modulated beam.

6. The method according to claim 1, wherein said directing step comprises directing the other optical path through a gas correlation cell containing a high density of the gas of interest.

7. The method according to claim 1, wherein said directing step comprises directing the two optical paths along approximately equal optical path lengths.

8. A gas filter correlation radiometer for determining the concentration of a gas of interest in a particular quantity from a polarized light beam which has passed through the gas of interest in the particular quantity, comprising:

a polarization modulator for modulating the polarized light beam between two alternating orthogonal polarization components;

a first polarization beam splitter for switching the modulated beam by transmitting one orthogonal polarization component of the polarization modulated light beam along a first optical path and reflecting the other orthogonal polarization component of the polarization modulated light beam along a second optical path;

a vacuum cell located in one of the first and second optical paths;

a spectral notch filter having spectral notches which are coincident with the band structure of the gas of interest, said spectral notch filter being located in the other of the first and second optical paths;

means for intersecting the two optical paths at an intersection point;

a second polarization beam splitter located at the intersection point of the first and second optical paths, said second polarization beam splitter transmitting one orthogonal component of the intersected components and reflecting the other orthogonal component, whereby a polarization modulated beam is formed comprising the two orthogonal components in alternate order; and an intensity detector for sensing a difference in the intensity between the two orthogonally polarized components of the formed beam as an indication of the spectral emission/absorption of the light by the gas of interest in the particular quantity, the spectral emission/absorption being indicative of the concentration of the gas of interest in the particular quantity.

9. The gas filter correlation radiometer according to claim 8, further comprising an optical polarizer for polarizing an incoming light beam prior to modulation by said polarization modulator.

10. The gas filter correlation radiometer according to claim 9, wherein said optical polarizer is selected from the group consisting of prism, reflection, dichroic and wire grid polarizers.

11. The gas filter correlation radiometer according to claim 8, wherein said intersecting means comprises a respective reflecting mirror arranged in each of the two optical paths.

12. The gas filter correlation radiometer according to claim 11, wherein the first beam splitter transmits horizontally polarized light and reflects vertically polarized light.

13. The gas filter correlation radiometer according to claim 12, wherein the second beam splitter transmits horizontally polarized light and reflects vertically polarized light.

14. The gas filter correlation radiometer according to claim 12, wherein the gas correlation cell is located along the first optical path and the vacuum cell is located along the second optical path.

15. The gas filter correlation radiometer according to claim 8, wherein both said first and said second polarization beam splitters transmit the same orthogonal component of the beam and reflect the same orthogonal component of the beam.

16. The gas filter correlation radiometer according to claim 8, wherein said first and second polarization beam splitters are selected from the group consisting of prism, reflector, and wire grid beam splitters.

17. The gas filter correlation radiometer according to claim 8, wherein said polarization modulator is selected from the group consisting of electro-optic, magneto-optic and photo-elastic modulators and liquid crystal devices.

18. The gas filter correlation radiometer according to claim 8, further comprising a spectral filter for filtering an incoming light beam prior to modulation by said polarization modulator.

19. The gas filter correlation radiometer according to claim 8, wherein said spectral notch filter comprises a gas correlation cell containing a high density of the gas of interest.

20. The gas filter correlation radiometer according to claim 8, wherein said intersecting means is located such that the optical lengths of each optical path from said first polarization beam splitter to the intersection point are approximately equal.

21. The gas filter correlation radiometer according to claim 8, further comprising a spectral filter for spectrally filtering the light beam prior to said polarization modulator to transmit only the portion of the optical spectrum of the beam which contains the transition lines of the gas of interest.

* * * * *